Figure 10:
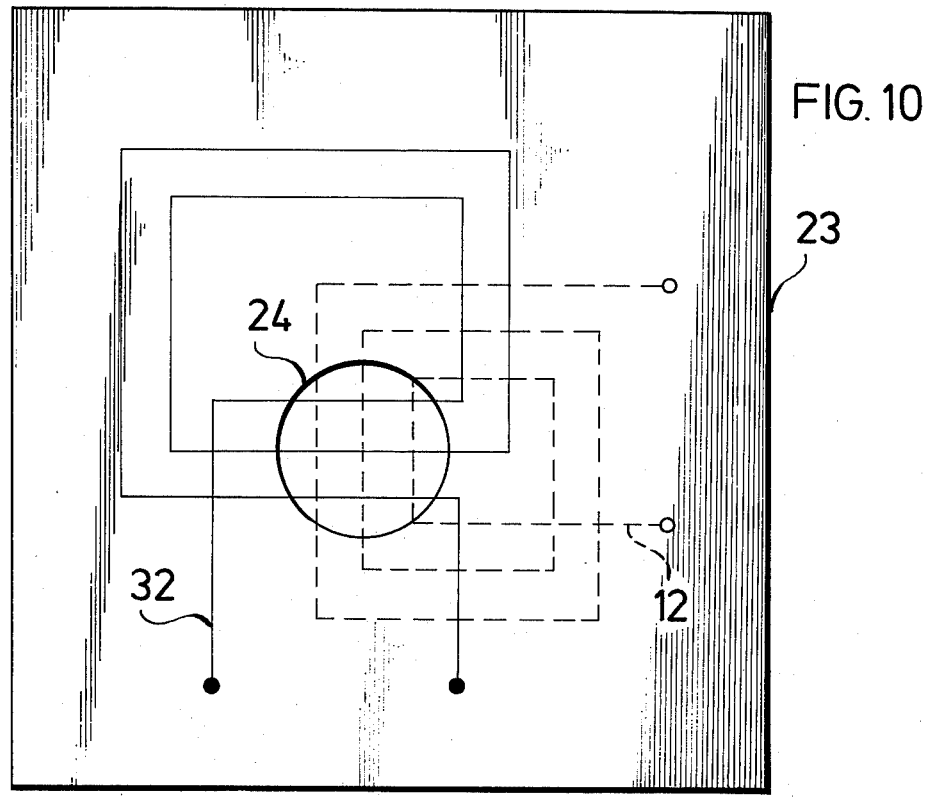

United States Patent [19]
Böttcher et al.

[11] 4,149,421
[45] Apr. 27, 1979

[54] DEVICE FOR UTRASONICALLY CHECKING MATERIAL BY MEANS OF AN ELECTRODYNAMIC CONVERTER

[75] Inventors: Wolfgang Böttcher; Hermann-Josef Kopineck, both of Dortmund, Fed. Rep. of Germany

[73] Assignee: Hoesch Werke Aktiengesellschaft, Dortmund, Fed. Rep. of Germany

[30] Foreign Application Priority Data

Nov. 27, 1976 [DE] Fed. Rep. of German .. 26.53923

[22] Filed: Nov. 28, 1977
[51] Int. Cl.² .......................................... G01N 29/04
[52] U.S. Cl. ........................................................ 73/643
[58] Field of Search ................. 73/643; 324/237, 238; 340/15

[56] References Cited

U.S. PATENT DOCUMENTS

| | | | |
|---|---|---|---|
| 3,583,213 | 6/1971 | Houck | 73/643 |
| 3,786,672 | 9/1972 | Gaerttner | 73/643 |

FOREIGN PATENT DOCUMENTS 376127 5/1973 U.S.S.R. .................................... 73/643

*Primary Examiner*—James J. Gill
*Attorney, Agent, or Firm*—Walter Becker

[57] ABSTRACT

A device for checking materials by means of an electrodynamic converter which includes a magnet and at least one high frequency coil arranged between the core of the magnet and the workpiece. The high frequency coil includes a first section effective with regard to the generation of ultra sound, and a second section which is not effective with regard to the generation of ultra sound. In the first section the individual currents in the windings of the high frequency coil have approximately the same direction while the second section is located outside the magnetic field of the magnet or opposite the workpiece behind a shielding.

10 Claims, 11 Drawing Figures

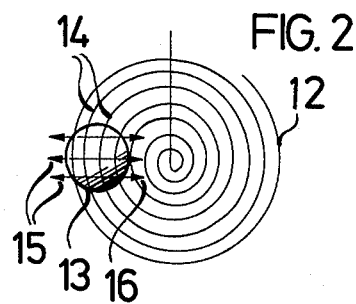
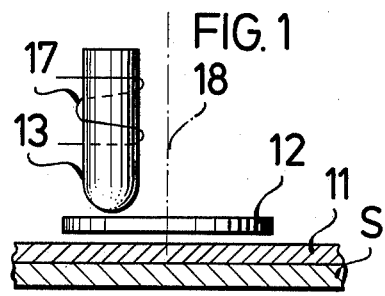
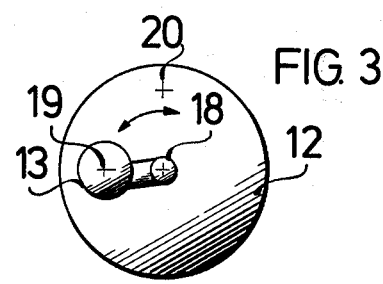
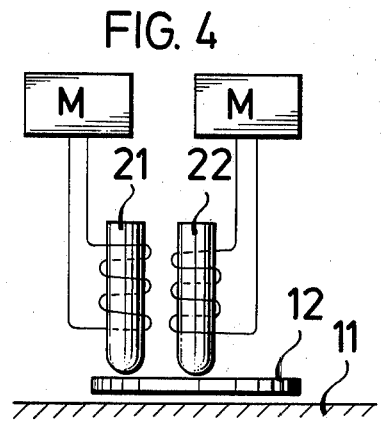
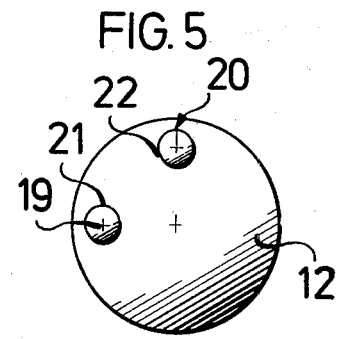

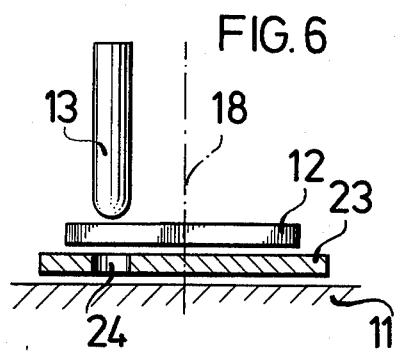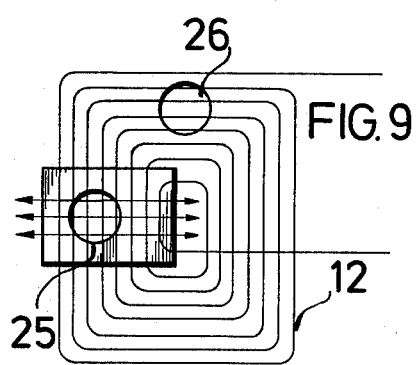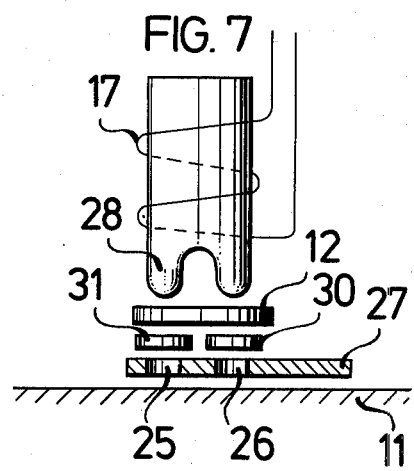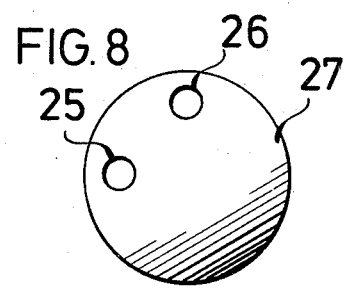

U.S. Patent  Apr. 17, 1979  Sheet 3 of 3  4,149,421

DEVICE FOR UTRASONICALLY CHECKING MATERIAL BY MEANS OF AN ELECTRODYNAMIC CONVERTER

The present invention relates to a device for testing materials by means of an electrodynamic converter which comprises a magnet and at least one high frequency coil located in the space between the core of the magnet and the workpiece.

It is an object of the invention so to change the heretofore known electrodynamic converter that it will be possible by the converter to generate polarized ultra sound waves.

Heretofore it was not possible by means of electrodynamic converters to generate free ultra sound waves which means linear polarized ultra sound waves not influenced by boundary surfaces, so that the advantages of such polarized ultra sound waves, particularly by the advantages caused by the missing coupling fluid, over the piezoelectric ultra sound generators could not be applied to all fields of use.

Heretofore known electrodynamic converters employed a spirally wound flat coil for generating the high frequency alternating field. Such spirally wound flat coils have the drawback that distributions of the excitation for the ultra sound field occur the maxima and minima of which distributions are located on concentric circles, the common center of which is located on the extension of the coil axis. The direction of oscillations of the individual elements of the distribution of the excitation of the ultra sound field are all directed differently, and merely to a common center.

Such altra sound fields oscillating in different directions cannot be used for a great number of special instances of application, for instance for testing mechanical tensions in a workpiece, and are not suitable for investigating the location or orientation of flaws in the material. These special instances of application require linear polarized ultra sound waves.

More specifically, therefore, it is an object of the present invention to provide an electrodynamic converter by means of which an ultra sound field can be generated which has approximately the same direction everywhere with regard to the wave front of the distribution of the excitation, while the direction is also changeable.

These and other objects and advantages of the invention will appear more clearly from the following specification in connection with the accompanying drawings, in which:

FIGS. 1 and 2 diagrammatically illustrate a high frequency coil with a fixed core and a magnet.

FIG. 3 diagrammatically illustrates a core of the magnet which core is movable over the high frequency coil.

FIGS. 4 and 5 respectively diagrammatically illustrate in front view and in top view two fixedly arranged cores of two magnets which are offset relative to each other by 90° above the high frequency coil.

FIG. 6 diagrammatically shows a shielding with an opening which shielding is located between the high frequency coil and the workpiece.

FIGS. 7 and 9 respectively diagrammatically illustrate a shielding with openings offset by 90° and with coils above said openings.

FIG. 9 is a diagrammatical illustration of a high frequency coil with straight winding sections.

FIG. 10 diagrammatically illustrates two high frequency coils with straight winding sections arranged one above the other.

Figure 11:
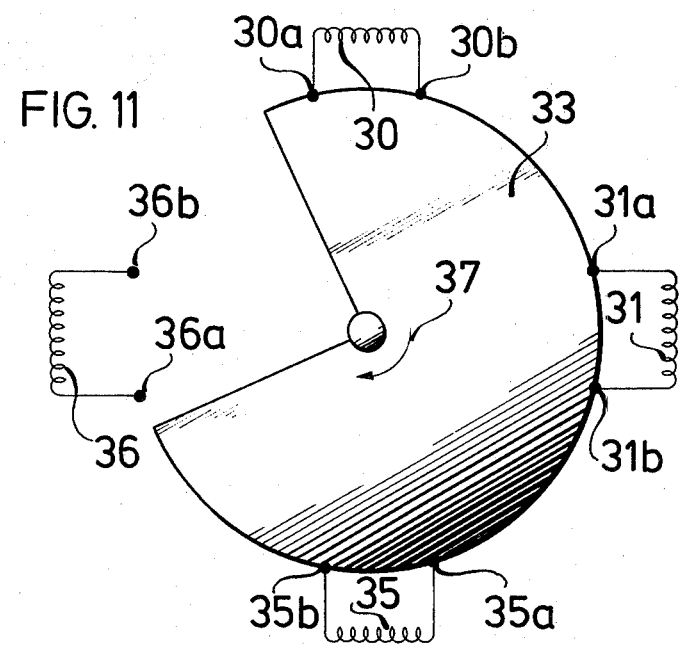

FIG. 11 illustrates a circuit according to which always the start and end of a winding of one coil are disconnected from each other while the start and the end of the remaining coils are short-circuited.

The device according to the present invention is characterized primarily in that the high frequency coil comprises a section which is effective with regard to the generation of ultra sound and furthermore comprises a noneffective section, while in the effective section the individual currents in the windings have approximately the same direction, and while the noneffective section is located outside the magnetic field of the magnet or is located opposite the workpiece behind a shield.

Thus, only by one section of the high frequency coil, ultra sound is created in the workpiece to be checked. In this only limited section of the high frequency coil the windings extend approximately in one direction so that the current passing through said windings generates a corresponding eddy current in the workpiece which in its turn generates a linear polarized ultra sound field because the eddy current is located in the region of the magnet. The remaining portions of the windings of the high frequency coil, the windings of which extend in part even in opposite direction to the winding of the effective section would generate an interfering ultra sound field. Therefore, the influence of the windings of the high frequency coil which extend in part in opposite direction to the windings of the effective section is prevented by the fact that they extend outside the magnetic field. In this way, strong Lorenz forces which generate the ultra sound waves in the workpiece can never act upon the eddy currents caused by the last mentioned windings of the high frequency coil.

There is a second possibility to prevent the undesired effect of the remaining portions of the high frequency coil onto the creation of the ultra sound. This second possibility consists in that between these parts of the high frequency coil and the workpiece there is provided a shielding, for instance a metal foil. As a result thereof, already in this metal foil the high frequency eddy currents will be generated. The workpiece which is located behind said shielding will substantially be free of eddy currents so that within this region also no ultra sound can be generated. If desired, also both steps may be simultaneously employed namely the shielding and only partial through-flow of the high frequency coil through the magnet. Further possibilities of employment for the device offer themselves when during the testing or checking operation, the direction of the emitted linearly polarized ultra sound waves can be changed. This is realized by an additional device sending out selectively linearly polarized ultra sound waves the direction of which form different angles with regard to the axes of the workpieces.

The simplest possibility to change the angle of the emitted linearly polarized ultra sound waves with regard to the workpiece consists in that the additional device consists of a rotatable device permitting a rotation of the testing or checking device relative to the workpiece.

The turning of the entire checking device has different drawbacks in view of the connecting cable. Furthermore, the turning can be effected only slowly so that this possibility is not suitable for fast checking operations. An improved embodiment is characterized primarily in that the additional device is so designed that by means of the latter different sections of the high frequency coil with different current directions of the windings for the generation of ultra sound can be employed one after another in the workpiece. This can be realized in a simple manner by permitting the displacement of the core of the magnet over a plurality of sections of the high frequency coil in different checking positions.

With a circular high frequency coil, the displacement is checked in a simplest manner by turning the core of the magnet about the axis of the high frequency coil. Inversely, also with a stationary core of the magnet, the high frequency coil may be displaced.

The described embodiment has the drawback that in view of its parts being mechanically displaceable, the device can be handled only relatively slowly, and, in view of the movable parts, disorders can easily occur. This drawback has been eliminated according to the present invention, namely by distributing a plurality of cores of magnets over the high frequency coil. These magnets are adapted to be magnetized one after the other so that those sections of the high frequency coil which are located within the region of said cores can one after another be employed for generating ultra sound in the workpiece. The customary high frequency coils are as a rule so small that only two or three cores of magnets can be distributed over the surface of said high frequency coils. According to the number of cores, only two or three possible directions of linearly polarized ultra sound waves are obtainable.

Still more directions of linearly polarized ultra sound waves are possible with small high frequency coils when as additional device a shielding with an opening left free for the effective section of the high frequency coil is movably arranged above the surface of the high frequency coil. Such shielding may consist of a thin metallic foil. The shielding has the advantage that only where it has an opening, the eddy currents induced by the high frequency coil can form in the workpiece. In order to generate another direction of the linearly polarized ultra sound wave, it is only necessary to displace the shielding with its opening, for instance by turning around the axis of the high frequency coil. Inasmuch as the shielding forms a very small part, the turning can be executed relatively fast. With this embodiment there is encountered the drawback that a rotatable or turnable shielding is more sensitive against mechanical damage than a nonmovable shielding cemented on foil. Another additional device is particularly well suitable for high checking or testing speeds on conveyor belts and their prevailing mostly rough conditions of operation. Such additional device comprises a shielding in which a plurality of openings have been left free and of which each opening is covered by a coil while a circuit is provided by means of which the start of the winding of a coil can with the end thereof be controlled in such a way that always the start and the end of the winding of a coil are separated and the start and the end of the remaining coils are short circuited.

The short circuited coil above the openings of the shielding, influence the magnetic alternating fields induced by the high frequency coil, in such a way as if the openings were not present and as if the shielding is also effected in the openings. Almost the entire energy which otherwise passes through the opening and causes eddy currents in the workpiece, is now employed for the formation of a short circuit current in the coil. This has an effect which is similar to the effect caused by the eddy currents in the shielding foil. If, however, the coils are not short circuited but the start and the end of the winding are open, the energy can pass through the coil and is able in the workpiece to induce eddy current necessary for the generation of ultra sound.

Practically no time is needed for opening and connecting the start and end of the coil. This is effected by known transistor circuits. It is advantageous when the effective section of the high frequency coil which is located in front of an opening of the shielding has rectilinear windings. In such an instance, the ultra sound field being generated is even more pronounced linearly polarized than is the case when the section consists of slightly bent windings of a spiral high frequency coil. Such rectilinear sections of the high frequency coil are obtained, as is well known, when the high frequency coil has been wound so as to form 3, 4, 6 or more corners.

For some testing or checking purposes, an additional improvement is obtained when during the checking or testing with two polarized ultra sound waves, these waves are generated precisely at the same spot of the workpiece. A generation at precisely the same spot is realized by having two high frequency coils, which are adapted to be turned on separately, with their effective sections, located one upon the other when looking in the checking direction, while each of the high frequency coils has another direction of the windings.

Referring now to the drawings in detail, and FIG. 1 thereof in particular, the workpiece 11 rests on the support S, and the high frequency coil 12 and the core 13 of the magnet 17 are located above the workpiece 11. That end of the core 13 of magnet 17 which faces the workpiece 11 is arranged over only a small section of the total surface of high frequency coil 12. In this section, all windings have approximately the same direction, as is shown in FIG. 2. The windings of this section induce eddy currents in the workpiece. In view of the magnetic field of the magnet 17, Lorenz forces act upon the eddy currents in the workpiece and generate ultra sound waves which have an oscillation corresponding to the directions 15 and 16. The magnet 17 is adpated with its core 13 to rotate also about the axis 18 of the high frequency coil 12 (see FIG. 3). A checking of the workpiece may be effected for instance when the core 13 has just reached its position 19. The next checking may be effected when the core 13 has reached a position 20. The linearly polarized ultra sound waves generated in position 20 have a direction of oscillation which forms an angle of 90° with the direction of oscillation of the ultra sound waves in the position 19. Thus, polarized ultra sound waves of any desired direction may be generated.

In FIGS. 4 and 5, the stationary magnets 21 and 22 are arranged in the positions 19 and 20. These magnets 21 and 22 are alternately energized as a result of which each time the direction of oscillation of the laterally polarized ultra sound waves are turned by 90°.

According to FIG. 6 the effective section of the high frequency coil 12 is additionally confined by the shielding 23 which has an opening 24 for the effective section.

In order to be able to generate another direction of oscillation of the linearly polarized ultra sound wave, the shielding 23 and the core 13 of the magnet may rotate together about the axis 18 similar to the principle illustrated and described in connection with FIG. 3. However, also with this embodiment, the core 13 may be stationarily arranged and may be so designed that it covers the entire surface of the high frequency coil 12 so that the latter will be penetrated all over by the magnetic lines of flux of the magnet. With such a design, only the shielding 23 will rotate.

According to FIGS. 7 and 8, the reference numerals 25 and 26 designate two openings of the stationary shielding 27 which openings are offset to each other by 90°. One portion of the core 28 of the strong magnet 17 is located over both openings. Instead of dividing the core 28 into two parts, also two independent magnets may be arranged above the openings 25 and 26.

Between the high frequency coil 12 and the openings 25 and 26 of the shielding 27 there are located the flat coils 30 and 31. The start and the end of the coil 31 are interconnected by means of a non-illustrated control device when for the coil 30 the start and the end are electrically separated from each other. Inversely, the control device short-circuits the coil 30 when the start and the end of the coil 31 are separated from each other.

According to the same principle, also more than two openings may be provided in the shieldings, which also are covered by the coils in conformity with the coils 30 and 31.

The generated ultra sound field is particularly precisely polarized when the openings 25 and 26 are located in front of precisely rectilinearly extending windings of the high frequency coil 12. This can be realized when the high frequency coil is wound in conformity with FIG. 9 so as to define rectangles.

FIG. 10 shows the high frequency coils 12 and 32 with their straight or rectilinear windings offset by 90° over the opening 24 of the shielding 23. As will be seen from FIG. 10, the shielding 23 with opening 24 is located above the workpiece to be checked, and the coil 12 is located above the shielding 23, and coil 32 is located on the top, i.e. still above coil 12. Of course, the high frequency coils 12 and 32 may have their windings offset with regard to each other by other angles. The high frequency coil 12 is turned on when the coil 32 is turned off and vice versa. The ultra sound field is generated only by the respectively turned-on high frequency coil. If a mixture of two linearly polarized ultra sound waves of different direction is to be generated, also both high frequency coils may be turned on simultaneously. Of course, the two high frequency soils 12 and 32 can be turned on simultaneously by mechanical switches or by reversing the plugging of the coil start and coil end.

FIG. 11 shows the same coils 30 and 31 which are seen in FIG. 7. In order to indicate that also more than two coils can be employed, FIG. 11 also shows the coils 35 and 36. FIG. 11 represents a mechanical switch. The electrically conductive metallic disc 33 has a non-electrically conductive cut-out which in the specific example shown in FIG. 11 amounts to about ¼ of the disc surface and is located just in front of coil 36. Coil start 36a and coil end 36b are thus electrically separated from each other. The coil start and coil end of the respective remaining coils 30, 31 and 35 are short-circuited by the metallic disc 33. Disc 33 can be rotated further in the direction of the arrow 37 so that subsequently the coil start 30a and the coil end 30b will be electrically separated from each other and coil 36 will be short-circuited. Correspondingly, by further turning the disc 33, the contacts of the respective remaining coils can be opened or short-circuited. Instead of the mechanical switch of FIG. 11, also an electronic switch may be employed.

It is, of course, to be understood that the present invention is, by no means, limited to the specific showing in the drawings, but also comprises any modifications within the scope of the appended claims.

What we claim is:

1. A checking device for checking materials by means of an electrodynamic converter, which includes: a magnet having a core, supporting means for receiving and supporting the material to be checked, a high frequency coil arranged between said core and said supporting means while being spaced from said supporting means so as to allow placing material to be checked between said high frequency coil and said supporting means, said high frequency coil comprising a first section effective in cooperation with said magnet to generate ultra sound waves in material placed between said supporting means and said first section of said high frequency coil, said first section of said high frequency coil being defined by the projection of said magnet onto said high frequency coil, said high frequency coil also comprising a second section arranged outside the magnetic field of said magnet whereby it is not effective to generate ultra sonic waves, the individual currents in the windings of said first section when said high frequency coil is energized having about the same direction, and shielding means arranged between said high frequency coil and said supporting means in spaced relationship to the latter with a predetermined surface being kept free of said shielding means to permit the insertion of material to be checked between said shielding means and said supporting means.

2. A device according to claim 1, which includes two individually energizable high frequency coils each having a first section effective for ultrasonic generation in magnetic field of said magnet, said first section when viewed in checking direction being located one above the other, the windings of said high frequency coils respectively having different directions.

3. A checking device for checking materials by means of an electrodynamic converter, which includes: a magnet having a core, supporting means for receiving and supporting the material to be checked, a high frequency coil arranged between said core and said supporting means while being spaced from said supporting means so as to allow placing material to be checked between said high frequency coil and said supporting means, said high frequency coil comprising a first section effective in cooperation with said magnet to generate ultra sound waves in material placed between said supporting means and said first section of said high frequency coil, said first section of said high frequency coil being defined by the projection of said magnet onto said high frequency coil, said high frequency coil also comprising a second section arranged outside the magnetic field of said magnet whereby it is not effective to generate ultra sonic waves, the individual currents in the windings of said first section when said high frequency coil is energized having about the same direction, and additional means supplemental to though including therewith parts of said first section and operable selectively to emit linearly polarized ultra sound waves which have different angles with regard to the axes of the material to be checked.

4. A device according to claim 3, in which said additional means includes a rotatable mechanism for rotating said checking device high frequency coil relative to the material to be checked.

5. A device according to claim 3, in which said additional means is operable by means of different sections of said high frequency coil with different current directions of the high frequency coil windings rotatable circularly of coil axis successively to generate ultra-sound waves in the material to be checked.

6. A device according to claim 5, in which as additional means said core of said magnet is displaceable over a plurality of sections of high frequency coil into different checking positions.

7. A device according to claim 5, in which as additional means said high frequency coil is displaceably arranged below said core of said magnet.

8. A device according to claim 5, which includes a plurality of magnets each having a core, and in which the cores of a plurality of magnets are distributed over said high frequency coil, a plurality of magnetizing means being provided for selectively successively magnetizing said cores whereby those sections of said high frequency coil which are located within the region of said cores are successively able to generate ultra sound waves in the material to be checked.

9. A device according to claim 5, in which said additional means includes a shield arranged below said high frequency coil and having an opening therethrough and adapted to be aligned with and arranged above said first section, said shield being movable over the surface of said high frequency coil.

10. A device according to claim 5, in which said additional means includes shielding provided with a plurality of openings, said device also comprising additional coils respectively arranged above said plurality of openings, and control means operable to bring about interruption of the start and the end of the winding of one of said additional coils while causing a short circuit between the start and the end of the winding of the other additional coils.

* * * * *

UNITED STATES PATENT OFFICE
CERTIFICATE OF CORRECTION

Patent No. 4149421                    Dated Apr. 17, 1979

Inventor(s) Wolfgang Böttcher and Hermann-Josef Kopineck

It is certified that error appears in the above-identified patent and that said Letters Patent are hereby corrected as shown below:

On the cover sheet insert

-- [21] Appl. No.: 855,289 --.

*Signed and Sealed this*

*Seventh* Day of *August 1979*

[SEAL]

*Attest:*

*Attesting Officer*

LUTRELLE F. PARKER
*Acting Commissioner of Patents and Trademarks*